United States Patent
Archibald et al.

[11] Patent Number: 6,159,157
[45] Date of Patent: Dec. 12, 2000

[54] BLOOD PRESSURE MEASUREMENT DEVICE WITH A SENSOR LOCATOR

[75] Inventors: G. Kent Archibald, Vadnais Heights; Timothy Curran, Ramsey; Orland H. Danielson, Roseville; Marius O. Poliac, St. Paul; Roger C. Thede, Afton, all of Minn.

[73] Assignee: Medwave, Inc., Arden Hills, Minn.

[21] Appl. No.: 09/299,222

[22] Filed: Apr. 23, 1999

[51] Int. Cl.$^7$ .................................................. A61B 5/00
[52] U.S. Cl. ........................ 600/485; 600/500; 600/503
[58] Field of Search .......................... 600/485, 500–503, 600/561

[56] References Cited

U.S. PATENT DOCUMENTS

| | | | |
|---|---|---|---|
| 4,307,727 | 12/1981 | Haynes | 128/672 |
| 4,799,491 | 1/1989 | Eckerle | 128/672 |
| 4,830,017 | 5/1989 | Perry et al. | 128/672 |
| 4,836,213 | 6/1989 | Wenzel et al. | 128/672 |
| 4,901,733 | 2/1990 | Kaida et al. | 128/687 |
| 4,928,702 | 5/1990 | Cousin | 128/678 |
| 4,993,422 | 2/1991 | Hon et al. | 128/672 |
| 5,033,471 | 7/1991 | Yokoe et al. | 128/681 |
| 5,163,438 | 11/1992 | Gordon et al. | 128/677 |
| 5,238,000 | 8/1993 | Niwa | 128/689 |
| 5,240,007 | 8/1993 | Pytel et al. | 128/672 |
| 5,243,992 | 9/1993 | Eckerle et al. | 128/690 |
| 5,263,484 | 11/1993 | Martin et al. | 128/672 |
| 5,271,405 | 12/1993 | Boyer et al. | 128/672 |
| 5,284,150 | 2/1994 | Butterfield et al. | 128/672 |
| 5,351,694 | 10/1994 | Davis et al. | 128/672 |
| 5,406,952 | 4/1995 | Barnes et al. | 128/672 |
| 5,450,852 | 9/1995 | Archibald et al. | 128/672 |
| 5,497,779 | 3/1996 | Takaya et al. | 128/672 |
| 5,640,964 | 6/1997 | Archibald et al. | 128/672 |
| 5,642,733 | 7/1997 | Archibald et al. | 128/672 |
| 5,649,542 | 7/1997 | Archibald et al. | 128/681 |
| 5,722,414 | 3/1998 | Archibald et al. | 128/672 |
| 5,738,103 | 4/1998 | Poliac | 128/672 |
| 5,797,850 | 8/1998 | Archibald et al. | 600/494 |
| 5,832,924 | 11/1998 | Archibald et al. | 128/672 |

*Primary Examiner*—Robert L. Nasser
*Attorney, Agent, or Firm*—Kinney & Lange, P. A.

[57] ABSTRACT

A blood pressure measurement device with a sensor locator for placing a non-invasive blood pressure measurement device over an underlying artery, the sensor locator having a plurality of extending fingers spaced from each other coupled to the non-invasive blood pressure measurement device.

15 Claims, 7 Drawing Sheets

BLOOD PRESSURE MEASUREMENT DEVICE WITH A SENSOR LOCATOR

BACKGROUND OF THE INVENTION

The present invention relates to systems for measuring arterial blood pressure. In particular, the invention relates to a method and apparatus for conveniently positioning a non-invasive blood pressure measurement device over an underlying artery for accurate measurement.

Blood pressure has been typically measured by one of four basic methods: invasive, oscillometric, auscultatory and tonometric. The invasive method, otherwise known as an arterial line (A-Line), involves insertion of a needle into the artery. A transducer connected by a fluid column is used to determine exact arterial pressure. With proper instrumentation, systolic, mean and diastolic pressure may be determined. This method is difficult to set up, is expensive and involves medical risks. Set up of the invasive or A-line method poses problems. Resonance often occurs and causes significant errors. Also, if a blood clot forms on the end of the catheter, or the end of the catheter is located against the arterial wall, a large error may result. To eliminate or reduce these errors, the set up must be adjusted frequently. A skilled medical practitioner is required to insert the needle into the artery. This contributes to the expense of this method. Medical complications are also possible, such as infection or nerve damage.

The other methods of measuring blood pressure are non-invasive. The oscillometric method measures the amplitude of pressure oscillations in an inflated cuff. The cuff is placed against a cooperating artery of the patient and thereafter pressurized or inflated to a predetermined amount. The cuff is then deflated slowly and the pressure within the cuff is continually monitored. As the cuff is deflated, the pressure within the cuff exhibits a pressure versus time waveform. The waveform can be separated into two components, a decaying component and an oscillating component. The decaying component represents the mean of the cuff pressure while the oscillating component represents the cardiac cycle. The oscillating component is in the form of an envelope starting at zero when the cuff is inflated to a level beyond the patient's systolic blood pressure and then increasing to a peak value where the mean pressure of the cuff is equal to the patient's mean blood pressure. Once the envelope increases to a peak value, the envelope then decays as the cuff pressure continues to decrease.

Systolic blood pressure, mean blood pressure and diastolic blood pressure values can be obtained from the data obtained by monitoring the pressure within the cuff while the cuff is slowly deflated. The mean blood pressure value is the pressure on the decaying mean of the cuff pressure that corresponds in time to the peak of the envelope. Systolic blood pressure is generally estimated as the pressure on the decaying mean of the cuff prior to the peak of the envelope that corresponds in time to where the amplitude of the envelope is equal to a ratio of the peak amplitude. Generally, systolic blood pressure is the pressure on the decaying mean of the cuff prior to the peak of the envelope where the amplitude of the envelope is 0.57 to 0.45 of the peak amplitude. Similarly, diastolic blood pressure is the pressure on the decaying mean of the cuff after the peak of the envelope that corresponds in time to where the amplitude of the envelope is equal to a ratio of the peak amplitude. Generally, diastolic blood pressure is conventionally estimated as the pressure on the decaying mean of the cuff after the peak where the amplitude of the envelope is equal to 0.82 to 0.74 of the peak amplitude.

The auscultatory method also involves inflation of a cuff placed around a cooperating artery of the patient. Upon inflation of the cuff, the cuff is permitted to deflate. Systolic pressure is indicated when Korotkoff sounds begin to occur as the cuff is deflated. Diastolic pressure is indicated when the Korotkoff sounds become muffled or disappear. The auscultatory method can only be used to determine systolic and diastolic pressures.

Because both the oscillometric and the auscultatory methods require inflation of a cuff, performing frequent measurements is difficult. The frequency of measurement is limited by the time required to comfortably inflate the cuff and the time required to deflate the cuff as measurements are made. Because the cuff is inflated around a relatively large area surrounding the artery, inflation and deflation of the cuff is uncomfortable to the patient. As a result, the oscillometric and auscultatory methods are not suitable for long periods of repetitive use.

Both the oscillometric and auscultatory methods lack accuracy and consistency for determining systolic and diastolic pressure values. The oscillometric method applies an arbitrary ratio to determine systolic and diastolic pressure values. As a result, the oscillometric method does not produce blood pressure values that agree with the more direct and generally more accurate blood pressure values obtained from the A-line method. Furthermore, because the signal from the cuff is very low compared to the mean pressure of the cuff, a small amount of noise can cause a large change in results and result in inaccurate measured blood pressure values. Similarly, the auscultatory method requires a judgment to be made as to when the Korotkoff sounds start and when they stop. This detection is made when the Korotkoff sound is at its very lowest. As a result, the auscultatory method is subject to inaccuracies due to low signal-to-noise ratio.

The fourth method used to determine arterial blood pressure has been tonometry. The tonometric method typically involves a transducer including an array of pressure sensitive elements positioned over a superficial artery. Hold down forces are applied to the transducer so as to flatten the wall of the underlying artery without occluding the artery. The pressure sensitive elements in the array typically have at least one dimension smaller than the lumen of the underlying artery in which blood pressure is measured. The transducer is positioned such that at least one of the individual pressure sensitive elements is over at least a portion of the underlying artery. The output from one of the pressure sensitive elements is selected for monitoring blood pressure. The pressure measured by the selected pressure sensitive element is dependent upon the hold down pressure used to press the transducer against the skin of the patient. These tonometric systems measure a reference pressure directly from the wrist and correlate this with arterial pressure. However, because the ratio of pressure outside the artery to the pressure inside the artery, known as gain, must be known and constant, tonometric systems are not reliable. Furthermore, if a patient moves, recalibration of the tonometric system is required because the system may experience a change in gains. Because the accuracy of these tonometric systems depends upon the accurate positioning of the individual pressure sensitive element over the underlying artery, placement of the transducer is critical. Consequently, placement of the transducer with these tonometric systems is time-consuming and prone to error.

The oscillometric, auscultatory and tonometric methods measure and detect blood pressure by sensing force or displacement caused by blood pressure pulses as the underlying artery is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood pressure pulses create a pressure gradient across the pressure sensitive elements. This uneven pressure gradient creates at least two different pressures, one pressure at the edge of the pressure sensitive element and a second pressure directly beneath the pressure sensitive element. As a result, the oscillometric, auscultatory and tonometric methods produce inaccurate and inconsistent blood pressure measurements.

There has been a continuing need for devices which will measure blood pressure non-invasively, with accuracy comparable to invasive methods. Medwave, Inc. the assignee of the present invention, has developed non-invasive blood pressure measurement devices which are described in the following United States patents: U.S. Pat. No. 5,649,542 entitled CONTINUOUS NON-INVASIVE BLOOD PRESSURE MONITORING SYSTEM; U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,720,292 entitled BEAT ONSET DETECTOR; U.S. Pat. No. 5,738,103 entitled SEGMENTED ESTIMATION METHOD; U.S. Pat. No. 5,722,414 entitled CONTINUOUS NON-INVASIVE BLOOD PRESSURE MONITORING SYSTEM; U.S. Pat. No. 5,642,733 entitled BLOOD PRESSURE SENSOR LOCATOR; and U.S. Pat. No. 5,797,850 entitled METHOD AND APPARATUS FOR CALCULATING BLOOD PRESSURE OF AN ARTERY. Further description of these devices is found in U.S. patent application Ser. No. 08/912,139 filed Aug. 15, 1997, entitled HAND-HELD NON-INVASIVE BLOOD PRESSURE MEASUREMENT DEVICE.

As described in these patents and the pending patent application, the Medwave non-invasive blood pressure measurement device and method determines blood pressure by sensing pressure waveform data derived from an artery. A pressure sensing device includes a sensing chamber with a diaphragm which is positioned over the artery. A transducer coupled to the sensing chamber senses pressure within the chamber. A flexible body conformable wall is located adjacent to (and preferably surrounding) the sensing chamber. The wall is isolated from the sensing chamber and applies force to the artery while preventing pressure in a direction generally parallel to the artery from being applied to the sensing chamber.

As varying pressure is applied to the artery by the sensing chamber, pressure waveforms are sensed by the transducer to produce sensed pressure waveform data. The varying pressure may be applied automatically in a predetermined pattern, or may be applied manually.

The sensed pressure waveform data is analyzed to determine waveform parameters which relate to the shape of the sensed pressure waveforms. One or more blood pressure values are derived based upon the waveform parameters. The Medwave blood pressure measurement devices include both automated devices for continually monitoring blood pressure (such as in a hospital setting) and hand-held devices which can be used by a physician, or by a patient when desired. These devices represent an important improvement in the field of non-invasive blood pressure measurement. Still further improvements, specifically with respect to convenient and accurate placement of the measurement device over an underlying artery, are highly desirable.

BRIEF SUMMARY OF THE INVENTION

The present invention is a blood pressure measurement device with a sensor locator for placing a non-invasive blood pressure measurement device over an underlying artery, the sensor locator having an guide coupled to the non-invasive blood pressure measurement device.

In a preferred embodiment of a hand-held blood pressure measurement device, the extending guide of the sensor locator includes two fingers that are positioned adjacent to and extend beyond a sensor interface assembly of the measurement device. The fingers are connected to a locator ring, which is coupled to a housing of the measurement device and is free to rotate with respect to the housing of the measurement device.

In a preferred embodiment of a continual blood pressure measurement device, the sensor locator is a generally U-shaped member that includes a locator pad integrally bridging a pair of extending fingers. The sensor locator is positioned adjacent to a sensor interface assembly and is connected to a holddown assembly via slidable pins.

DETAILED DESCRIPTION

Figure 1:
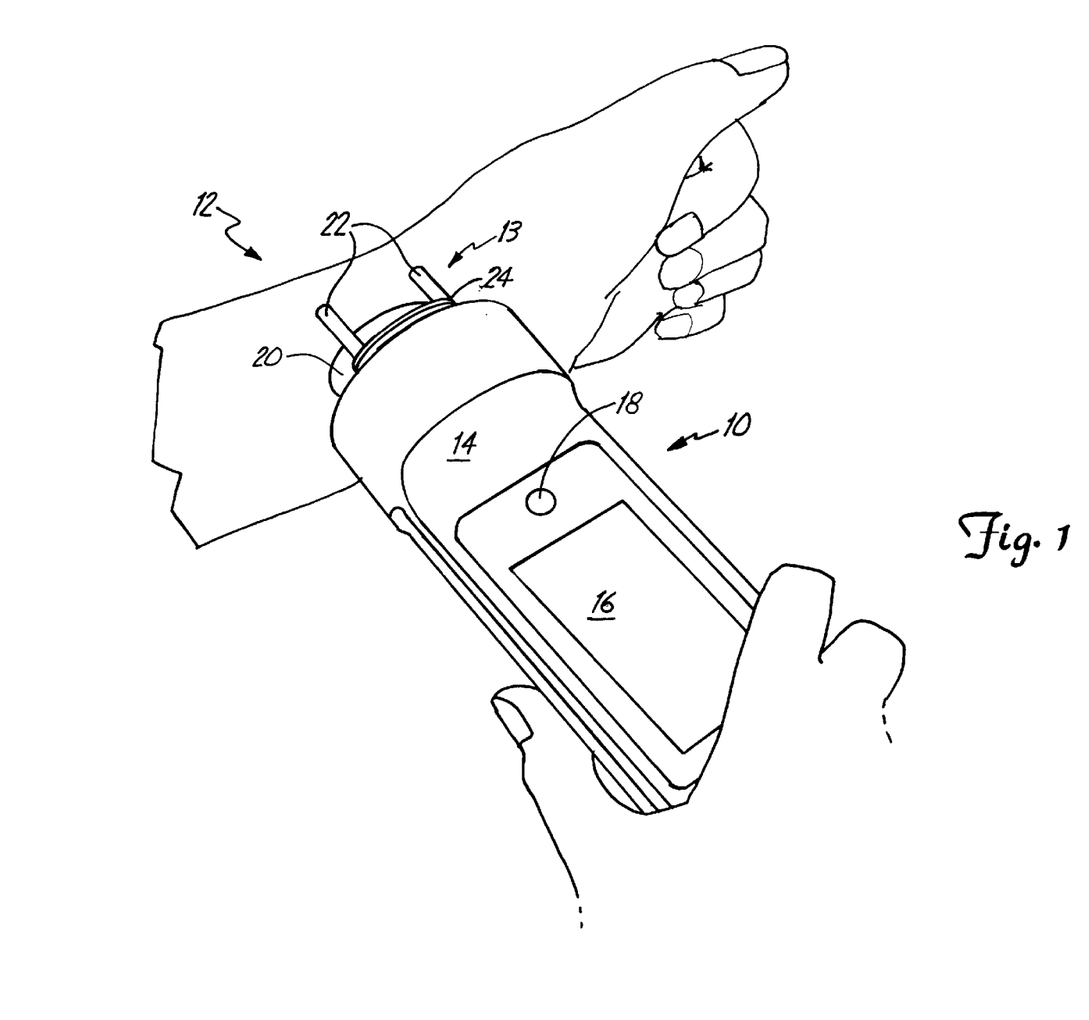
FIG. 1 is a perspective view of a first embodiment of a hand-held blood pressure measurement device incorporating the locator feature of the present invention positioned over the wrist of a patient.

FIG. 1 illustrates a hand-held blood pressure measurement device being used to measure and display blood pressure within an underlying artery within wrist 12 of a patient. Using sensor locator 13 of measurement device 10, measurement device 10 is placed at the projection of the styloid process bone perpendicular to wrist 12. A small amount of force is manually applied to the radial artery, which runs along the styloid process bone. As the force is manually applied, cardiac pressure waveforms are recorded and the blood pressure calculated. Blood pressure measurement device 10 includes sensor locator 13, main housing 14, display panel 16, power 18, and sensor interface assembly 20. Sensor locator 13 includes locator fingers 22 and locator bridge 24.

Housing 14 contains all of the electrical components of measurement device 10. The diameter and length of housing 14 allow it to be easily held by a user (either medical personnel or the patient) during the measurement process. The holddown force is applied by applying force in an axial direction to wrist 12. The applied force is transmitted from housing 14 to sensor interface assembly 20.

Display panel 16 is preferably a liquid crystal display (LCD). In a preferred embodiment, display panel 16 simultaneously displays the following values based upon blood pressure measurements: systolic pressure, diastolic pressure, pulse rate, and mean blood pressure. Display panel 16 also preferably provides visual prompting for manually applying a varying holddown pressure.

Power switch 18 is actuated to turn on power to the circuitry within housing 14. Timing circuitry within housing 14 automatically turns power off after a predetermined period of inactivity. Actuation of switch 18, after the unit is turned on, causes the display to indicate previous readings of blood pressure and pulse rate. In one embodiment there are ten memory locations for readings that can be displayed.

Sensor interface assembly 20 is pivotally mounted to housing 14. As pressure is manually applied by moving housing 14 in an axial direction to wrist 12 toward the artery, that force is transferred from housing 14 to sensor interface assembly 20.

Locator fingers 22 of sensor locator 13 are elongated cylindrical extensions. Preferably, there are two locator fingers 22 and they are spaced from each other as well as from sensor interface assembly 20. Sensor locator 13 is mounted within housing 14 so as to allow locator fingers to freely rotate about sensor interface assembly 20. Locator bridge 24 is press fit onto locator fingers 22. Locator bridge 24 is arch shaped and provides stability to locator fingers 22. Locator bridge 24 also helps to maintain a constant separation between locator fingers 22.

In operation, sensor interface assembly 20 is positioned over the radial artery by placing locator fingers 22 of sensor locator 13 on either side of the projections of the styloid process bone. With locator fingers 22 straddling the projection of the styloid process bone, a user brings sensor interface assembly 20 into contact with wrist 12 of the patient by applying an axial force on housing 14, while keeping the axial direction of housing 14 correctly oriented with respect to wrist 12. Placing locator fingers 22 on either side of the styloid process bone ensures that the sensor interface assembly 20 of measuring device 10 is properly positioned directly over the targeted radial artery. The user then begins to apply a varying force to the artery by applying axial force from housing 14 to sensor interface assembly 20.

The force applied to the artery is swept in an increasing fashion so the pressure waveform data from a series of pulses are obtained with different amounts of force being applied. To achieve the desired pattern of variable force, user feedback is preferably provided with device 10. The process of applying force in response to audible tones and/or visual movable bars on display 16 is fully described in U.S. patent application Ser. No. 09/174,164, entitled "Non-Invasive Blood Pressure Sensor With Motion Artifact Reduction", and is incorporated herein.

Instead of having to palpate wrist 12 to identify the location of the radial artery, a user simply places device 10 adjacent wrist 12 so that locator fingers 22 of sensor locator 13 straddle the projection of the styloid process bone. The measurement process is significantly simplified with the present invention.

Figure 2:
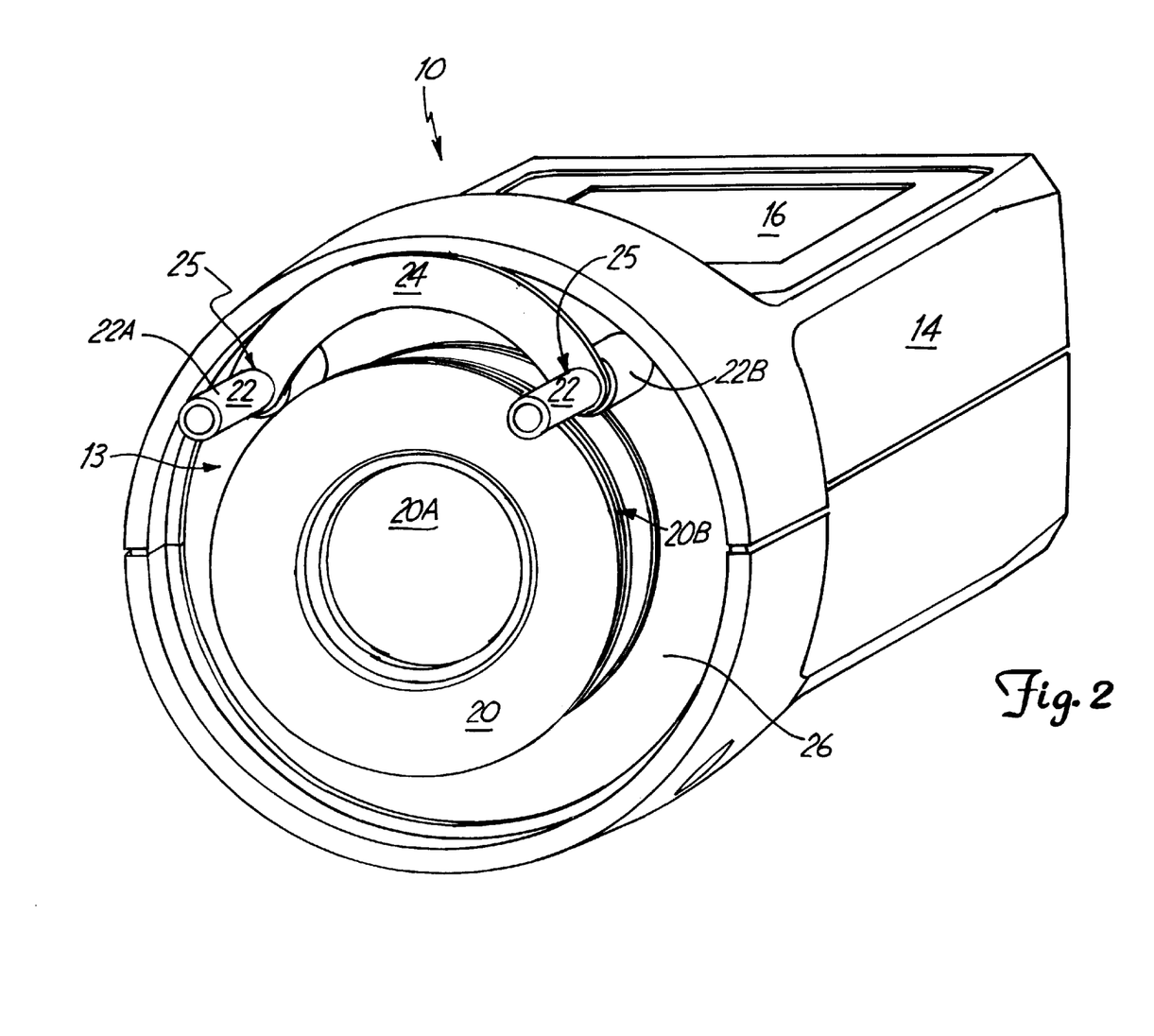
FIG. 2 shows in more detail the locator feature of the hand-held blood pressure measurement device of FIG. 1.

FIG. 2 is a perspective view showing the front of measurement device 10. As can be seen in FIG. 2, sensor locator 13 further includes locator ring 26. Locator ring 26 connects sensor locator 13 to main housing 14. Locator ring 26 is an annular ring that is held by main housing 14 so that locator ring 26 can freely rotate about sensor interface assembly 20. Locator fingers 22 are fixed to locator ring 26 and thus follow the rotation of locator ring 26.

As can be seen in FIG. 2, each locator finger 22 includes forward section 22A and rear section 22B. Forward section 22A of locator finger 22 has a smaller diameter than rear section 22B. Forward section 22A of locator finger 22 contacts the patient's anatomy while the rear section 22B does not. Locator bridge 24 includes apertures 25 that have a diameter large enough to accommodate forward sections 22A of locator fingers 22. Locator bridge 24 is press fit onto locator fingers 22 until bridge 24 engages rear section 22B of locator fingers 22. Locator bridge 24 provides structural support to locator fingers 22.

The operation of the sensor interface assembly 20 is substantially disclosed in the above identified U.S. patent application Ser. No. 09/174,164 (herein incorporated by reference) and assigned to Medwave, Inc. Generally, sensor interface assembly 20 preferably includes an active portion 20A and a sidewall 20B for sensing blood pressure pulses of the underlying artery. Sensor interface assembly 20 interfaces between the underlying artery and a sensor (not shown) such as a transducer to calculate the blood pressure of the underlying artery based upon signals produced by the measurement device 10.

Figure 3:
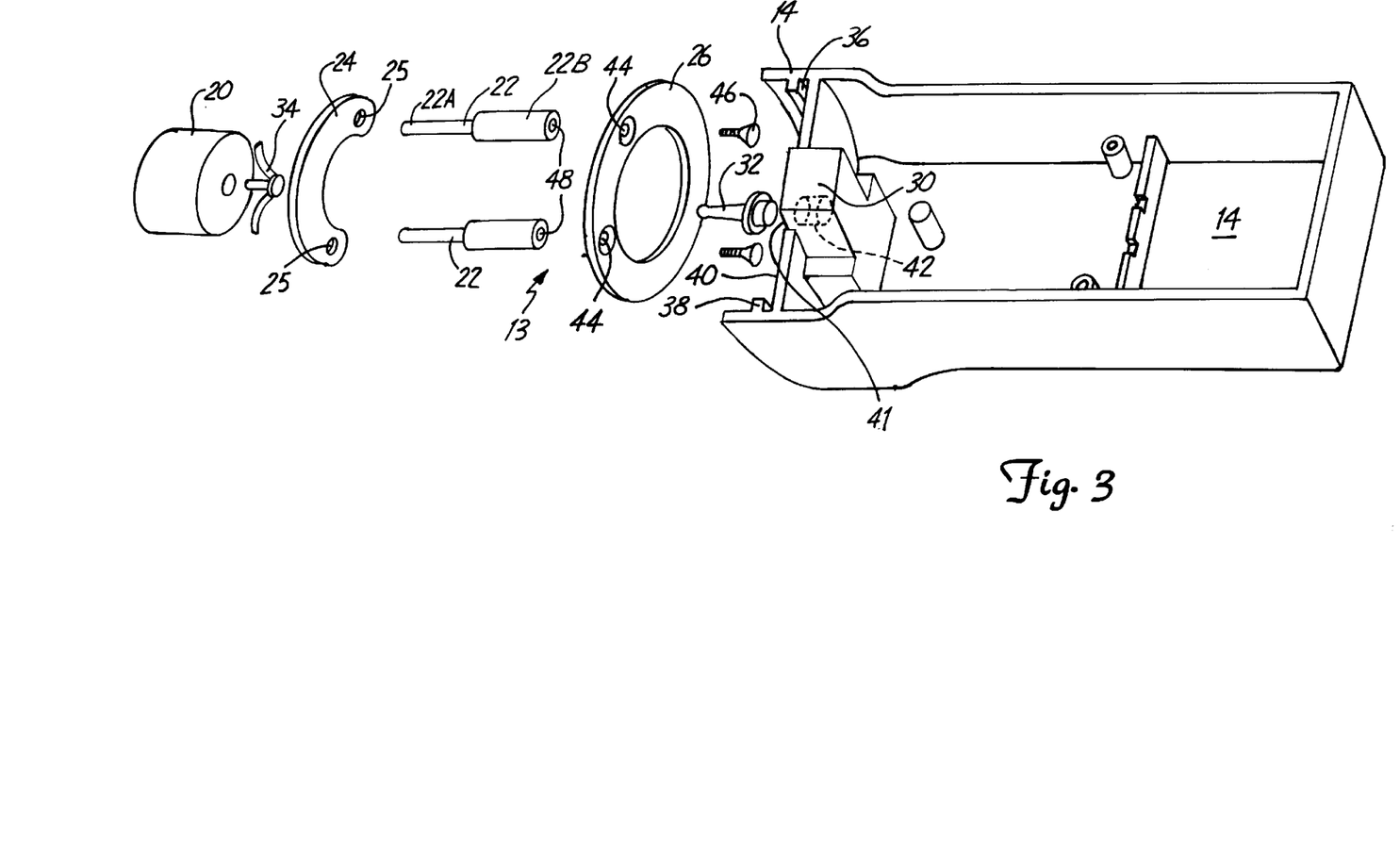
FIG. 3 is a partial exploded view of the hand-held blood pressure measurement device of FIG. 1.

FIG. 3 is a partial exploded view (with top half of main housing 14 and the electrical components from main housing 14 removed for clarity) that best illustrates the relationship of sensor locator 13 to main housing 14. Measuring device 10 further includes mounting housing 30, mounting stem 32, and spring 34. Main housing 14 further includes groove 36 formed between annular lip 38 and retaining wall 40.

Mounting housing 30 is molded in main housing 14 and includes front face 41 which lies flush with a front surface of retaining wall 40. Mounting housing 30 includes cavity 42 in front face 41 of mounting housing 30 that extends partially through mounting housing 30. Mounting stem 32 is press fit into cavity 42 of mounting assembly 30. Spring 34 rests on mounting stem 32 and sensor interface assembly 20 is mounted onto mounting stem 32 so that sensor interface assembly 20 is pivotally coupled to mounting stem 32 and engages spring 34. Spring 34 allows sensor interface assembly 20 to pivot when engaging a patient's anatomy while biasing sensor interface assembly 20 to its default position aligned in the axis of main housing 14.

Locator ring 26 includes bores 44, which are preferably tapered so that a rear face of bore 44 has a larger diameter than a forward face of bore 44. Each tapered bore 44 accommodates screw 46 so that the head of screw 46 engages the tapered walls of bore 44. Each of locator fingers 22 includes threaded bore 48. Threaded bore 48 of each locator finger 22 is of approximately the same diameter as the forward face of each bore 44 of locator ring 26. Threaded bore 48 of each locator finger 22 is aligned with respective bore 44 of locator ring 26 so that screw 46 can fasten each locator finger 22 to locator ring 26.

Locator ring 26 is inserted into groove 36 of main housing 14. Annular lip 38 and retaining wall 40 retain locator ring 26 while allowing locator ring 26 to rotate freely within groove 36. Bores 44 of locator ring 26 are positioned away from the outer diameter of locator ring 26 so that they are spaced from annular lip 38. Thus, locator fingers 22, when attached, avoid contact with annular lip 38 and do not interfere with the rotation of sensor locator 13.

In a preferred embodiment, to accomplish proper straddling of the protrusion of the styloid process bone, locator fingers 22 of sensor locator 13 are spaced an inch apart as measured between the centers of bores 46 of locator ring 26. Proper placement of active portion 20A of sensor interface assembly 20 over the radial artery is achieved by spacing locator fingers 22 at a distance 0.47 in. (1.19 cm) away from the center of sensor interface assembly 20, as measured from a line connecting the centers of bores 44 of locator ring 26 to the center of bore 42 of mounting housing 30. The preferred embodiment automatically places the sensor of measurement device 10 over the underlying radial artery for accurate measurement of a patient's blood pressure.

Figure 4:
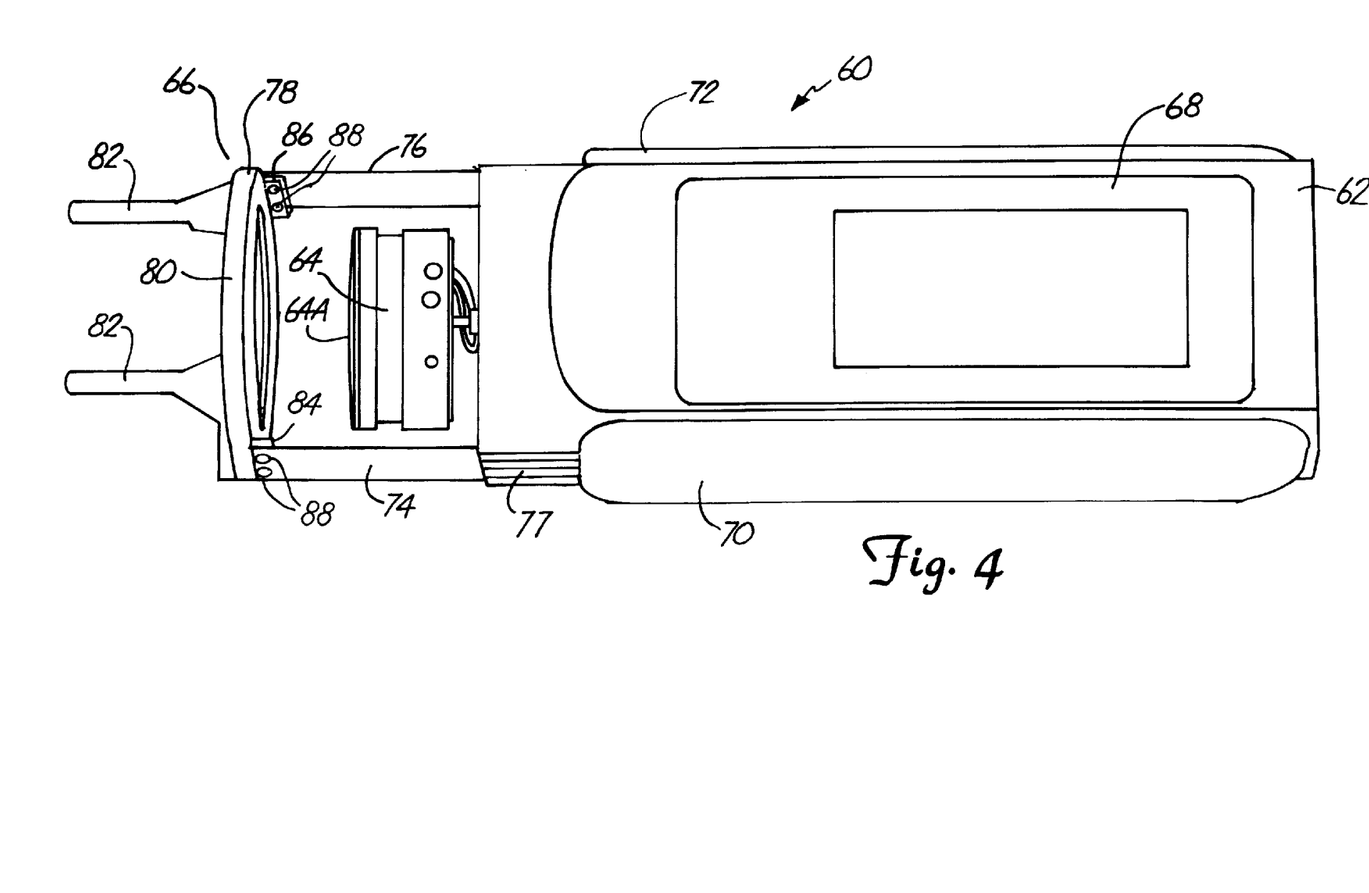
FIG. 4 is a perspective view of a second embodiment of a hand-held blood pressure measurement device including the locator feature of the present invention.

FIG. 4 is a perspective view illustrating a second embodiment of the present invention. Hand-held blood pressure measurement device 60 includes main housing 62, sensor interface assembly 64, sensor locator 66, display panel 68, and sensor locator support sleeves 70 and 72. Sensor locator 66 further includes slidable support members 74 and 76 each having slit 77, mounting ring 78, locator ring 80, and locator fingers 82.

As in the first embodiment (of FIGS. 1–3), main housing 62 of blood pressure measurement device 60 contains all of the electrical components of measurement device 60, and is designed to be easily held by a user during the measurement process. Display panel 68 is also preferably a liquid crystal display (LCD) that simultaneously displays the systolic pressure, diastolic pressure, pulse rate, mean blood pressure, and visual prompting for applying a varying holddown pressure.

Support sleeves 70 and 72 are mounted to main housing 62 and receive slidable support members 74 and 76, respectively. Slidable support members 74 and 76 are thin rectangular arms that slide in support sleeves 70 and 72, respectively, and each of members 74 and 76 contains slit 77 for containing a spring (not shown) that returns sensor locator 66 to its extended position, as shown. Slidable support members 74 and 76 support mounting ring 78, which is a thin annular ring with an outer diameter approximately equal to the diameter of a forward section of main housing 62 and an inner diameter large enough to accommodate passage over sensor interface assembly 64. Mounting ring 78 preferably includes flanges 84 and 86 for connecting mounting ring 78 to slidable support members 74 and 76. Preferably, screws 88 affix mounting ring 78 to slidable support members 74 and 76. As holddown pressure is applied by a user, mounting ring 78 is driven toward main housing 62 as slidable support members 74 and 76 recede into support sleeves 70 and 72, respectively. Mounting ring 78 continues past contacting surface 64A of sensor interface assembly 64 allowing sensor interface assembly 64 to contact the patient's anatomy to begin the measurement process.

Sensor locator 66 further includes locator ring 80 mounted onto mounting ring 78 so that locator ring 80 is allowed to freely rotate about mounting ring 78. Locator ring 80 is an annular ring with roughly the same inner and outer diameters as mounting ring 78. Locator fingers 82 are elongated cylindrical extensions that are integrally coupled to locator ring 80 and extend away from main housing 62. Preferably, a front face of locator ring 80 is tapered with the bottom of locator ring 80 being wider than the top (adjacent locator fingers 82). As with the first embodiment, locator fingers 82 of sensor locator 66 are placed on either side of the projection of the styloid process bone of the patient's wrist, and main housing 62 can be rotated so that display panel 68 faces a user while the position of locator fingers 82 is maintained. Sensor locator 66 guides a user to properly orient device 60 on the patient's wrist by placing ring 80 flat on the wrist.

Sensor locator 66 allows blood pressure measurement device 60 to be placed properly over the radial artery to accurately measure blood pressure of a patient. Sensor locator 66 of measurement device 60 allows for convenient measuring of a patient's blood pressure without requiring a user to first palpate and locate an appropriate artery. Instead, a user quickly and easily places measurement device 60 in position and accurately measures blood pressure values.

Figure 5A:
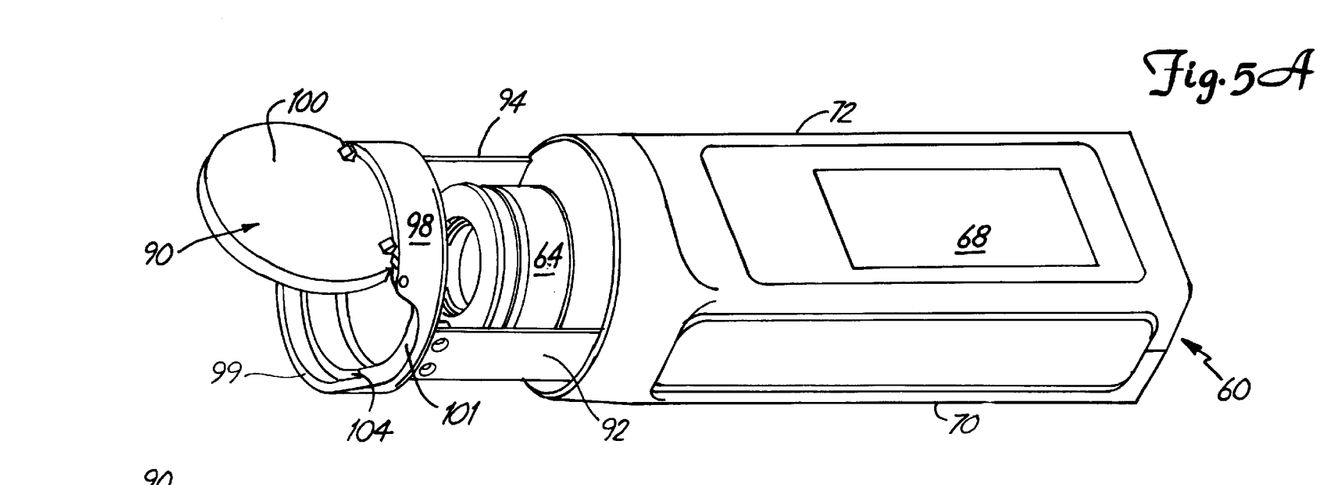
FIG. 5A is a top perspective view of a hand-held blood pressure measurement device including a third embodiment of the locator feature of the present invention.
Figure 5B:
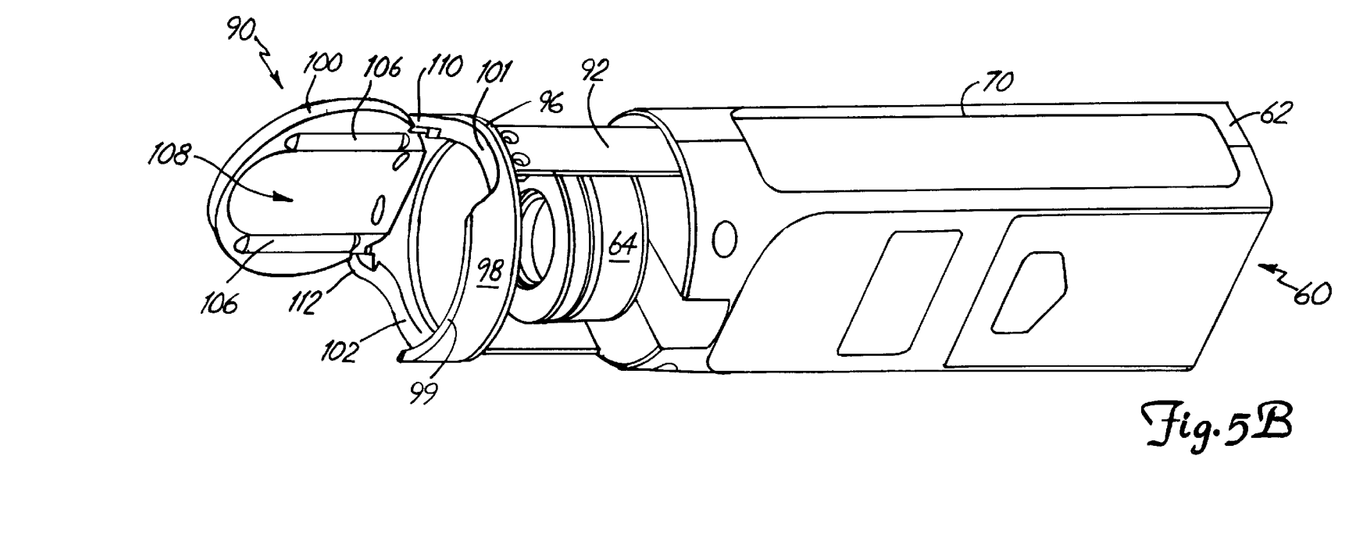
FIG. 5B is a bottom perspective view of the hand-held blood pressure measurement device of FIG. 5A.

FIGS. 5A and 5B illustrate a third embodiment of a sensor locator for a hand-held blood pressure measurement device. Blood pressure measurement device 60 includes main housing 62, sensor interface assembly 64, display panel 68 and support sleeves 70 and 72 as described with respect to the second embodiment illustrated in FIG. 4. However, sensor locator 90, illustrated in FIGS. 5A and 5B, includes slidable support members 92 and 94, mounting ring 96, locator base 98, and locator cap 100. Locator base 98 includes contact surface 99, recesses 101 and 102, and shoulder 104. Locator cap 100 includes locator guides 106 and depression 108.

Slidable support members 92 and 94 are thin rectangular members that are slidably coupled to main housing 62 via support sleeves 70 and 72 respectively. When a holddown force is applied by a user, slidable support members 92 and 94 retract into support sleeves 70 and 72, respectively, until sensor interface assembly 64 comes into contact with the anatomy of the patient. Mounting ring 96 is fixed to slidable support members 92 and 94. Mounting ring 96 is an annular ring with an outer diameter roughly equal to the diameter of main housing 62 and an inner diameter large enough to accommodate passage over sensor interface assembly 64.

Locator base 98 is connected to mounting ring 96 so that locator base 98 can freely rotate about mounting ring 96. Locator base 98 is a short tubular member with outer and inner diameters roughly equal to that of mounting ring 96. Locator base 98 facilitates placement of locator cap 100 and placement of measurement device 60 in proper orientation with the patient's wrist. Contact surface 99 is defined by a rim along an elevated section of the tubular sidewall of locator base 98. Contact surface 99 guides a user to place measurement device 60 at a proper angle to a surface of the patient's wrist.

Contact surface 99 is located between recesses 101 and 102, which are located on opposite sides of the tubular sidewall of locator base 98. Recesses 101 and 102 facilitate access to locator cap 100 when sensor locator 90 is in a closed position, and also assure that no force is applied to the underlying artery as sensor locator 90 is placed against the patient's wrist. Locator base 98 further includes annular shoulder 104 along the interior of its tubular sidewall. Annular shoulder 104 limits the movement of locator cap 100 and serves as the resting surface for locator cap 100 when sensor locator 90 is in the closed position.

Locator cap 100 is connected to locator base 98 via hinges 110 and 112. Hinges 110 and 112 are spring biased allowing locator cap 100 to open (as illustrated in FIGS. 5A and 5B)

and when not in use return locator cap 100 to the closed position (not shown). The bottom side of locator cap 100 (shown in FIG. 5B) includes locator guides 106 and depression 108. Locator guides 106 are longitudinal extensions of the bottom surface of locator cap 100. Locator guides 106 are placed on opposite sides of the protrusion of the styloid process bone to properly position sensor interface assembly 64 over the radial artery in the wrist of the patient. Depression 108 is located between locator guides 106 and accommodates the protrusion of the styloid process bone. Locator cap 100 is designed to accommodate the anatomy of the patient to properly locate measurement device 60 so that sensor interface assembly 64 can accurately measure the blood pressure within the radial artery of the patient.

Figure 6:
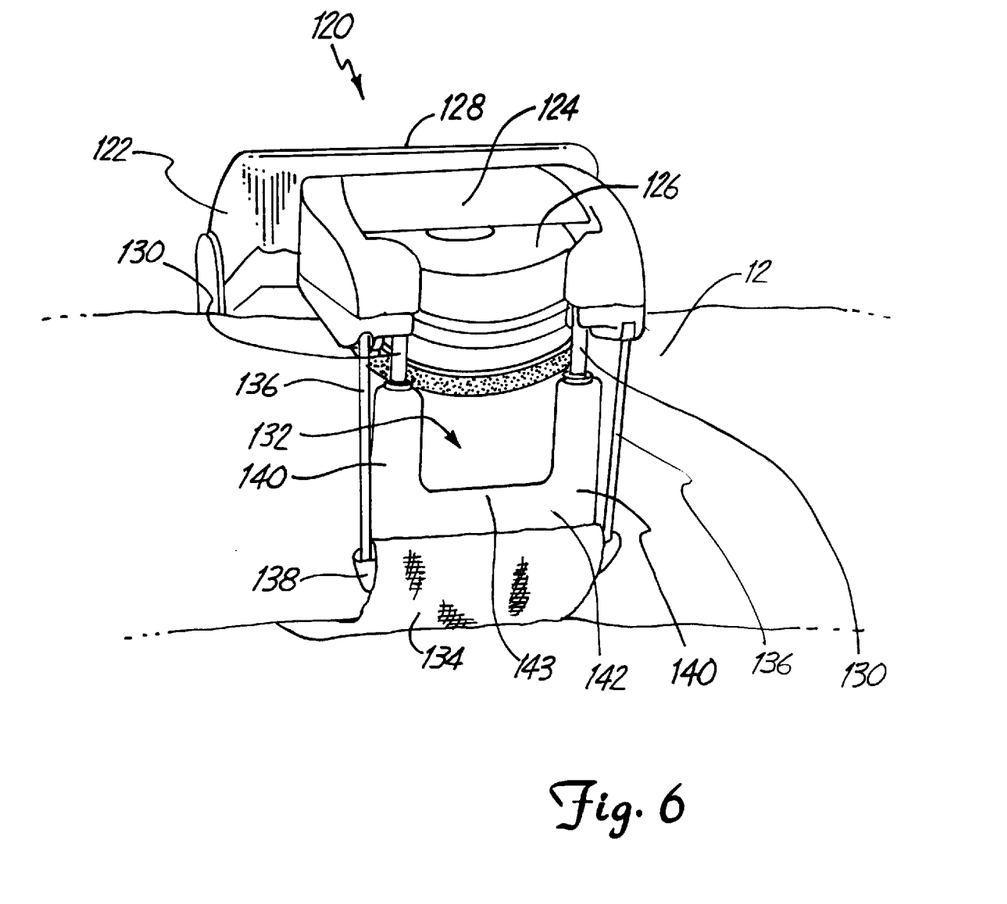
FIG. 6 is a perspective view of the preferred embodiment of a continual blood pressure measurement device incorporating the locator feature of the present invention positioned over the wrist of a patient.

FIG. 6 illustrates a continual blood pressure measurement device that incorporates the sensor locator feature of the present invention. The continual blood pressure measurement device is shown being used to measure blood pressure within an underlying artery within wrist 12 of a patient. Measurement device 120 includes holddown assembly 122, swivel mount 124, sensor interface assembly 126, electrical connector 128, slide pins 130, sensor locator 132, and wrist mount 134. Holddown assembly 122 includes cable 136 and swivel 138. Sensor locator 132 includes locator fingers 140 and locator pad 142.

A continual blood pressure device without the locator feature of the present invention is substantially disclosed in U.S. patent application Ser. No. 08/388,752 entitled WRIST MOUNTED BLOOD PRESSURE SENSOR (herein incorporated by reference) and assigned to Medwave, Inc. Generally, holddown assembly 122 causes sensor interface assembly 126 to apply varying pressure to the underlying artery of wrist 12. Holddown assembly 122 also regulates the tightness of wrist mount 134 about wrist 12 to control the holddown pressure and to prevent constriction of blood flow through wrist 12. Sensor interface assembly 126 interfaces between the underlying artery and a sensor (not shown) such as a transducer to calculate the blood pressure of the underlying artery based upon signals produced by the measurement device 120. Sensor interface assembly 126 is pivotally connected to holddown assembly 122 via swivel mount 124. Swivel mount 124 allows sensor interface assembly 126 to pivot near the wrist surface to accommodate the anatomy of a patient.

Holddown assembly 122 and wrist mount 134 maintain measurement device 120 on wrist 12 of the patient. Wrist mount 134 loops around swivel 138 and is tightened around wrist 12 until sensor interface assembly 126 contacts the anatomy of the patient. Holddown assembly 122 causes interface assembly 126 to apply pressure upon the underlying artery by articulation of cable 136 into holddown assembly 122. As cable 136 is drawn into holddown assembly 122, swivel 138 is pulled toward holddown assembly 122 and wrist mount 134 is tightened. The articulation of cable 136 and resultant tightening of wrist mount 134 causes sensor interface assembly 126 to apply a force on the underlying radial artery. Holddown assembly 122 controls the rate and amount of articulation of cable 136 and thus controls the amount and rate of the varying pressure.

In the preferred embodiment of the continual blood pressure measurement device, cable 136 includes an inner string covered in part by flexible tubing. Preferably the inner string enters holddown assembly 122 and is wound around a wind-up shaft (not shown). The wind-up shaft is controlled by a motor assembly (not shown) also contained in holddown assembly 122. Cable 136 is articulated by the motor assembly spinning the wind-up shaft and winding the inner string. As the inner string winds around the wind-up shaft and cable 136 is drawn into holddown assembly 122, the length of the exposed inner string of cable 136 outside of holddown assembly 122 is shortened and wrist mount 134 is tightened. Flexible tubing of cable 136 is preferably long enough to cover the exposed portion of the inner string of cable 136 outside of holddown assembly 122. Preferably, the flexible tubing of cable 136 extends into holddown assembly 122, but is not long enough to be wound around the wind-up shaft. The flexible tubing of cable 136 provides durability to cable 136 which incurs significant stress during the continual measurement process.

Electrical connection 128 electrically couples sensor interface assembly 126 with holddown assembly 122. Additionally, power for the sensor (not shown) such as a transducer, within sensor interface assembly 126 is delivered via electrical connection 128. Blood pressure waveform signals produced by sensor interface assembly 126 are communicated to an external control and display device (not pictured) using electrical connection 128.

Sensor locator 132, as described above with respect to other embodiments, positions measurement device 120 so that sensor interface assembly 126 lies directly over the radial artery running along the styloid process bone within wrist 12 of a patient. Sensor locator 132 is preferably a U-shaped member defined by the integral mold of locator pad 142 and locator fingers 140. Locator fingers 140 are cylindrical extensions with distal ends that extend toward locator pad 142. Locator fingers 140 and locator pad 142 are integrally formed so that locator pad 142 forms a distal extension of locator fingers 140 that bridges locator fingers 140. The U-shaped sensor locator 132 forms gap 143 between locator fingers 140.

In operation, gap 143 of sensor locator 132 is positioned over the protrusion of the styloid process bone with locator fingers 140 straddling the styloid process bone. Positioning sensor locator 132 over the styloid process bone causes sensor interfaces assembly 126 to be properly positioned over the underlying radial artery for accurate blood pressure measurement.

Sensor locator 132 is slidably connected to holddown assembly 122 via slide pins 130. Slide pins 130 are fixedly connected to holddown assembly 122, while being slidably coupled to locator fingers 140 of sensor locator 132. Each locator finger 140 includes a bore for receiving one of slide pins 130. As pressure is applied to the underlying artery (as cable 136 is drawn into holddown assembly 122 and wrist mount 134 tightened), sensor locator 132 maintains its position, straddling the protrusion of the styloid process bone, by allowing slide pins 130 to slide into the respective bores of locator fingers 140.

Figure 7:
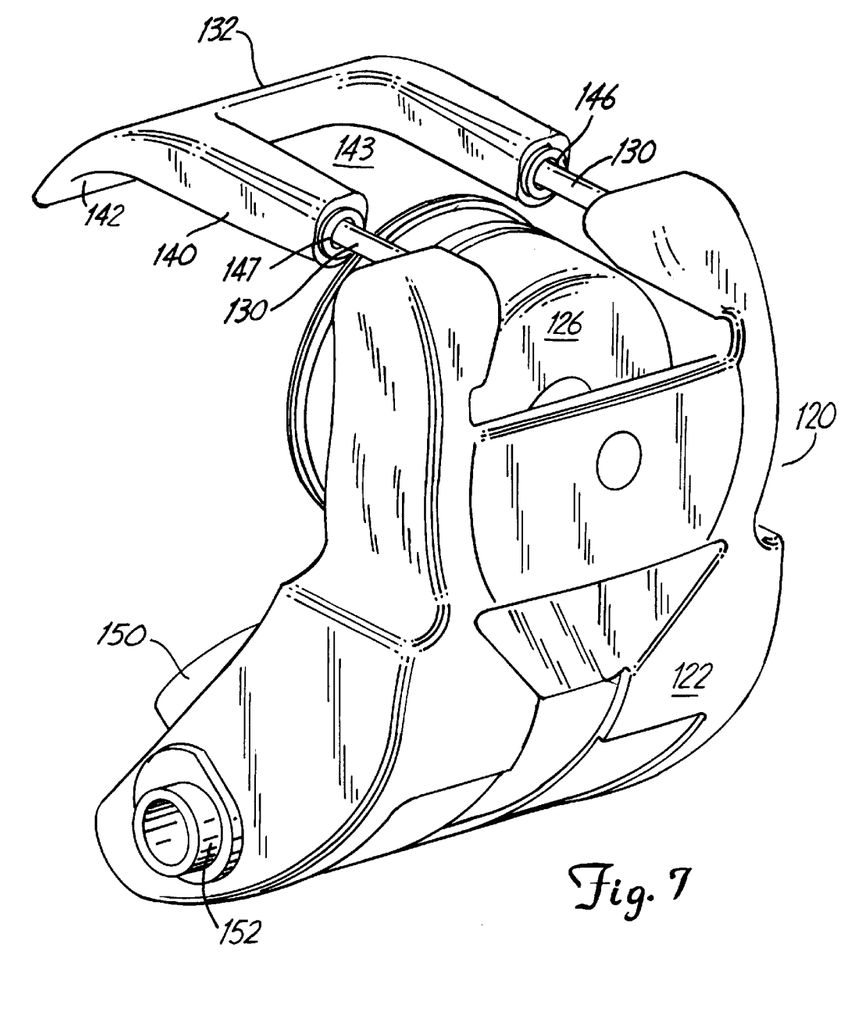
FIG. 7 is a perspective view of the continual blood pressure measurement device of FIG. 6 with certain holddown portions removed to better illustrate the locator feature of the present invention.

FIG. 7 shows continual blood pressure measurement device 120 with portions of holddown assembly 122 including cable 136 removed to better illustrate sensor locator 132. As is more clearly shown in FIG. 7, in addition to locator fingers 140, locator pad 142, and gap 143, sensor locator 132 also includes slide pin connectors 146 and 147. FIG. 7 also illustrates that measurement device 120 additionally includes wrist pads 150 (only a single wrist pad is shown) and electrical connector 152.

Locator pad 142 is preferably curved at its distal end to more securely contact a patients anatomy. Additionally, locator pad 142 consists preferably of flexible rubber. A flexible locator pad 142 is more comfortable to a patient and better accommodates the varying anatomies of patients. As can be better seen in FIG. 7, locator fingers 140 include slide pin connectors 146 and 147. Slide pin connectors 146 and 147 are press fit into the respective bores of locator fingers 140. Slide pin connectors 146 and 147 slidably receive slide pins 130. Preferably, slide pin connectors 146 and 147 are spring biased to maintain sensor locator 132 separated from holddown assembly 122.

Wrist pads 150 are configured for being positioned over and proximate to a surface of wrist 12. Wrist pads 150 support measurement device 120 adjacent to wrist 12 and provide additional comfort to a patient. Electrical connector 152 allows continual blood pressure measurement device 120 to communicate with an external control and display device (not shown). The control device instructs measurement device 120, via electrical connector 152, to begin the measurement process and controls the applied holddown pressure. Furthermore, the external control and display device receives the sensed blood pressure waveform signals via electrical connector 152 and records, processes and displays those signals as well as the systolic, mean, and diastolic blood pressures and a pulse rate.

The present invention allows a user to quickly and accurately initiate the blood pressure measurement process using a non-invasive blood pressure measurement device. The present invention removes the variables of first finding an underlying artery and then aligning the sensor of the measurement device with the underlying artery. Although the present invention has been described with reference to preferred embodiments, workers skilled in the art will recognize that changes may be made in form and detail without departing from the spirit and scope of the invention.

What is claimed is:

1. A locator for a non-invasive blood pressure measurement device, the locator comprising an extending guide adapted to be coupled to the non-invasive blood pressure measurement device the extending guide having a plurality of spaced guide members.

2. The locator of claim 1 wherein the plurality of spaced guide members guide includes a pair of fingers.

3. The locator of claim 2 further comprising a rotatable support member for connecting the pair of fingers to the non-invasive blood pressure measuring device.

4. The locator of claim 2 further comprising a support bridge coupling the pair of fingers.

5. A locator for a non-invasive blood pressure measurement device, the locator comprising:

a plurality of extending fingers spaced from each other; and means for connecting the plurality of extending fingers to the non-invasive blood pressure measurement device.

6. The locator of claim 5 wherein the coupling of the locator ring includes mounting the locator ring on a mounting ring, the mounting ring being connected to the pair of support members.

7. A locator for a non-invasive blood pressure measurement device, the locator comprising:

a pair of support members adapted to be slidably connected to the non-invasive blood pressure measuring device; and a locator ring having a pair of extending guide members spaced from each other coupled to the pair of support members.

8. The locator of claim 7 wherein the locator ring includes a contacting surface for orienting the non-invasive blood pressure measurement device relative to a wrist of a patient.

9. A locator for a non-invasive blood pressure measurement device, the locator comprising a U-shaped member having a pair of guides, the U-shaped member adapted to be coupled to the non-invasive blood pressure measurement device.

10. A locator for a non-invasive blood pressure measurement device, the locator comprising:

a pair of support members adapted to be connected to the non-invasive blood pressure measuring device;

a base member attached to the pair of support members; and a locating cap having a plurality of protruding guides coupled to the base member.

11. A method for measuring blood pressure using a non-invasive blood pressure measurement device, the method comprising:

placing a locator member along a side of a wrist of a patient, such that the locator member positions the non-invasive blood pressure measurement device over an underlying artery;

applying axial pressure on the non-invasive blood pressure measurement device;

sensing blood pressure; and calculating blood pressure values based on the sensed blood pressure.

12. The method of claim 11 further comprising orienting the non-invasive blood pressure measurement device relative to the wrist of the patient by placing a contacting surface of the locator member adjacent the wrist.

13. A non-invasive blood pressure measurement device for sensing blood pressure of an underlying radial artery of a patient, the device comprising:

a holddown assembly having a movable force applying member;

a sensor interface having a sensing surface for sensing arterial pressure; and locator means for positioning the sensing surface of the sensor interface over the underlying radial artery in reference to a wrist of the patient.

14. The device of claim 13 wherein the locator means is slidably coupled to the holddown assemby.

15. A non-invasive blood pressure measurement device, the device comprising:

means for applying pressure to an artery so that the artery exhibits pressure data;

sensing means for sensing the pressure data;

locator means for positioning the sensing means above the artery, the locator means having a guide with a plurality of spaced extensions adapted to contact a side of a wrist of a patient;

signal producing means connected to the sensing means for producing output signals corresponding to the sensed pressure data; and processing means for receiving the output signals from the signal producing means, for deriving a plurality of parameters using sensed pressure data and for determining a blood pressure value using the derived parameters.

* * * * *

UNITED STATES PATENT AND TRADEMARK OFFICE
CERTIFICATE OF CORRECTION

PATENT NO. : 6,159,157
DATED : December 12, 2000
INVENTOR(S) : G. Kent Archibald et al.

It is certified that error appears in the above-identified patent and that said Letters Patent is hereby corrected as shown below:

Column 12,
Line 43, delete "13", insert -- 12 --

Signed and Sealed this

Second Day of October, 2001

Attest:

NICHOLAS P. GODICI
Attesting Officer   Acting Director of the United States Patent and Trademark Office